(12) United States Patent
Seifert et al.

(10) Patent No.: US 11,813,468 B2
(45) Date of Patent: Nov. 14, 2023

(54) CONNECTOR CONDITIONING/BORE PLUG

(71) Applicant: Medtronic, Inc., Minneapolis, MN (US)

(72) Inventors: Kevin R. Seifert, Forest Lake, MN (US); Lonnie D. Ronning, Coon Rapids, MN (US); Michael D. Eggen, Chisago City, MN (US); Michelle S. Reinert, Isanti, MN (US)

(73) Assignee: Medtronic, Inc., Minneapolis, MN (US)

( * ) Notice: Subject to any disclaimer, the term of this patent is extended or adjusted under 35 U.S.C. 154(b) by 28 days.

(21) Appl. No.: 17/378,003

(22) Filed: Jul. 16, 2021

(65) Prior Publication Data

US 2023/0013928 A1 Jan. 19, 2023

(51) Int. Cl.
*A61N 1/375* (2006.01)
*H01R 13/62* (2006.01)

(52) U.S. Cl.
CPC .......... *A61N 1/3752* (2013.01); *H01R 13/62* (2013.01); *H01R 2201/12* (2013.01)

(58) Field of Classification Search
CPC ...... A61N 1/3752; A61N 1/376; A61N 1/372; A61N 1/362; A61N 1/36; A61N 1/0565; A61N 1/05; A61N 1/04
See application file for complete search history.

(56) References Cited

U.S. PATENT DOCUMENTS

| | | | | |
|---|---|---|---|---|
| 3,348,548 A | * | 10/1967 | Chardack | A61N 1/056 174/71 R |
| 3,760,810 A | * | 9/1973 | Van Hoorn | A61B 17/12013 606/140 |
| 5,676,688 A | * | 10/1997 | Jaker | A61M 25/0119 606/198 |
| 5,741,273 A | * | 4/1998 | O'Regan | A61B 17/12013 606/1 |
| 5,788,715 A | * | 8/1998 | Watson, Jr. | A61B 17/12013 606/140 |
| 5,823,961 A | * | 10/1998 | Fields | A61M 25/0105 604/524 |
| 6,321,126 B1 | | 11/2001 | Kuzma | |
| 6,895,276 B2 | * | 5/2005 | Kast | H01R 24/58 607/37 |
| 7,218,971 B2 | * | 5/2007 | Heil, Jr. | A61N 1/0568 607/121 |
| 7,997,854 B2 | | 8/2011 | LaRose et al. | |
| 8,419,609 B2 | | 4/2013 | Shambaugh, Jr. et al. | |
| 9,336,711 B2 | * | 5/2016 | Toyomura | G09G 3/3233 |
| 9,526,522 B2 | | 12/2016 | Wood et al. | |
| 9,533,082 B2 | | 1/2017 | Reichenbach et al. | |

(Continued)

FOREIGN PATENT DOCUMENTS

WO 2012128777 A1 9/2012

*Primary Examiner* — Harshad C Patel
(74) *Attorney, Agent, or Firm* — Shumaker & Sieffert, P.A.

(57) ABSTRACT

A bore plug for an implantable medical device. The bore plug includes an elongate body having a proximal portion, a distal portion, and defining a major longitudinal axis therethrough, the distal portion being sized and configured to be received within a bore of the implantable medical device. The distal portion includes a lubricating element configured to lubricate the bore when the distal portion is at least one from the group consisting of inserted within and withdrawn from the bore.

20 Claims, 4 Drawing Sheets

(56) References Cited

U.S. PATENT DOCUMENTS

| | | |
|---|---|---|
| 9,561,053 B2 | 2/2017 | Bonde et al. |
| 9,622,750 B2 * | 4/2017 | Chotenovsky ... A61B 17/12009 |
| 9,668,915 B2 * | 6/2017 | Haffner ................. A61F 9/0017 |
| 9,814,815 B2 | 11/2017 | McSweeney et al. |
| 9,867,621 B2 * | 1/2018 | Maurus ............ A61B 17/12013 |
| 9,943,294 B2 * | 4/2018 | Behymer ............... A61M 25/02 |
| 9,943,356 B2 | 4/2018 | Bloom et al. |
| 10,286,132 B2 | 5/2019 | McSweeney et al. |
| 10,300,286 B2 | 5/2019 | Ward et al. |
| 10,541,500 B2 | 1/2020 | Skubitz et al. |
| 10,813,789 B2 * | 10/2020 | Haffner ................. A61K 9/2072 |
| 2002/0072757 A1 * | 6/2002 | Ahmed ............ A61B 17/12013 |
| | | 606/139 |
| 2008/0208302 A1 * | 8/2008 | Alexander ........... A61N 1/0529 |
| | | 607/116 |
| 2009/0054941 A1 * | 2/2009 | Eggen ................. A61N 1/0565 |
| | | 607/9 |
| 2009/0198255 A1 * | 8/2009 | Ikeda ............... A61B 17/12013 |
| | | 606/140 |
| 2011/0160824 A1 * | 6/2011 | Ware ....................... A61N 1/05 |
| | | 607/116 |
| 2012/0034804 A1 * | 2/2012 | Smith ..................... F16F 1/045 |
| | | 439/345 |
| 2013/0123866 A1 * | 5/2013 | McDonald ........... A61N 1/3752 |
| | | 29/857 |
| 2015/0342875 A1 * | 12/2015 | Haffner ................. A61K 47/32 |
| | | 53/421 |
| 2016/0121106 A1 * | 5/2016 | Marshall ............. A61N 1/0504 |
| | | 607/119 |
| 2017/0105762 A1 * | 4/2017 | Bloom ............... A61B 17/3468 |
| 2018/0021171 A1 * | 1/2018 | Kahook ............... A61F 9/0026 |
| | | 607/53 |
| 2018/0036125 A1 | 2/2018 | Deshmukh et al. |
| 2018/0193008 A1 | 7/2018 | Behymer et al. |
| 2018/0280058 A1 * | 10/2018 | Meade ............... A61B 17/3468 |
| 2019/0070422 A1 * | 3/2019 | Regnier ............. A61N 1/37518 |
| 2019/0262570 A1 * | 8/2019 | Lee ................... A61M 16/0672 |
| 2019/0275294 A1 * | 9/2019 | Trösken ............. A61M 39/1011 |
| 2021/0154477 A1 * | 5/2021 | Asleson ............. A61N 1/3684 |

* cited by examiner

CONNECTOR CONDITIONING/BORE PLUG

CROSS-REFERENCE TO RELATED APPLICATION n/a.

FIELD

The present technology is generally related to bore plugs and connector conditioning for implantable medical devices.

BACKGROUND

Bore plugs are used to protect bores of implantable medical devices. Such bore plugs are inserted within the bores and are typically removed when a connector of the medical device is inserted within the bore. However, the force at which a clinician used to insert/withdraw connectors within corresponding bores is inconsistent. For example, too large of an insertion force used to insert a connector within the bore could cause the connected lead to buckle.

SUMMARY

The techniques of this disclosure generally relate to bore plugs and connector conditioning for implantable medical devices.

In one aspect, the present disclosure provides a bore plug for an implantable medical device. The bore plug includes an elongate body having a proximal portion, a distal portion, and defining a major longitudinal axis therethrough, the distal portion being sized and configured to be received within a bore of the implantable medical device. The distal portion includes a lubricating element configured to lubricate the bore when the distal portion is at least one from the group consisting of inserted within and withdrawn from the bore.

In another aspect of this embodiment, the distal portion is composed of silicone, and wherein the lubricating element is embedded within at least a portion of the silicone.

In another aspect of this embodiment, the lubricating element is a flexible ring extending outward from the distal portion.

In another aspect of this embodiment, the flexible ring is disposed proximal to a distal most end of the distal portion.

In another aspect of this embodiment, the proximal portion defines a first diameter and the distal portion defines a second diameter less than the first diameter.

In another aspect of this embodiment, the proximal portion defines at least one relief circumferentially disposed about the proximal portion.

In another aspect of this embodiment, the bore plug further includes a gripping element extending proximally from the proximal portion.

In another aspect of this embodiment, the gripping element is flexible.

In another aspect of this embodiment, the gripping element is substantially planar.

In another aspect of this embodiment, the gripping element extends in a direction substantially orthogonal to the major longitudinal axis.

In another aspect of this embodiment, the elongate body and the lubricating element are formed as a unitary body.

In another aspect of this embodiment, the bore plug further includes at least one flange surrounding at least a portion of the proximal portion.

In one aspect, a connector for an implantable medical device includes an elongate body having a proximal portion, a distal portion, the distal portion being sized and configured to be received within a bore of the implantable medical device and including a plurality of electrical contacts. The distal portion includes a lubricating element configured to lubricate the bore when the distal portion is at least one from the group consisting of inserted within and withdrawn from the bore.

In another aspect of this embodiment, the lubricating element is a flexible ring extending outward from the distal portion.

In another aspect of this embodiment, the flexible ring is disposed proximal to a distal most end of the distal portion.

In one aspect, a bore plug for an implantable medical device includes an elongate body having a proximal portion, a distal portion, and defining a major longitudinal axis therethrough, the distal portion being sized and configured to be received within a bore of the implantable medical device. The distal portion includes a lubricating element, the lubricating element including a flexible ring disposed proximal to a distal most end of the distal portion, the lubricating element being configured to lubricate the bore when the distal portion is withdrawn from the bore. A flexible gripping element extends proximally from the proximal portion, the gripping element being configured to twist and retain its original shape.

In another aspect of this embodiment, the proximal portion defines a first diameter and the distal portion defines a second diameter less than the first diameter, and wherein the proximal portion is sized to be received within the bore of the implantable medical device.

In another aspect of this embodiment, the gripping element extends in a direction substantially orthogonal to the major longitudinal axis.

In another aspect of this embodiment, the elongate body and the lubricating element are formed as a unitary body.

In another aspect of this embodiment, the bore plug further includes at least one flange surrounding at least a portion of the proximal portion.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

Figure 1:
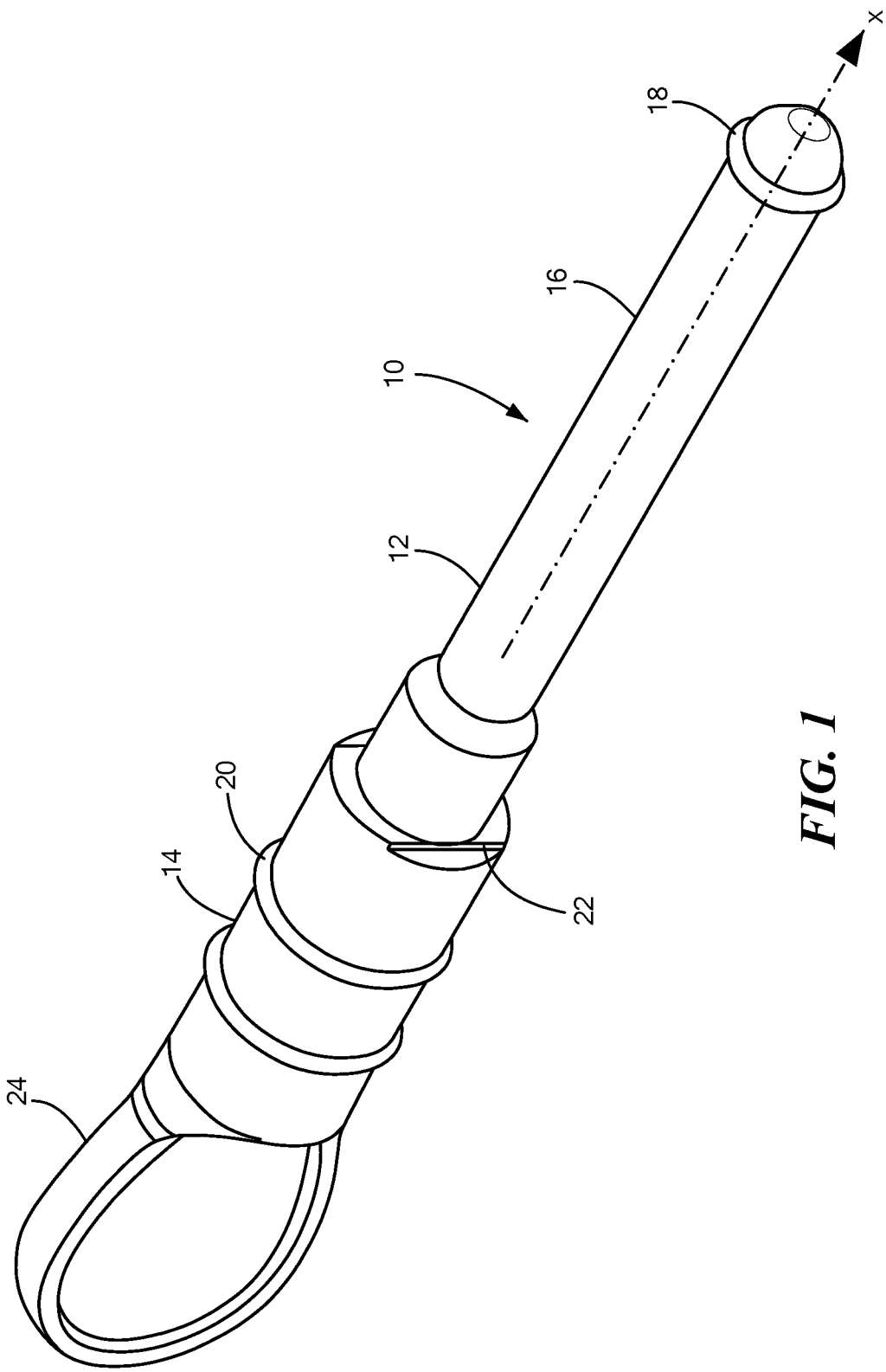
FIG. 1 is a front perspective view of a bore plug constructed in accordance with the principles of the present application.
Figure 2:
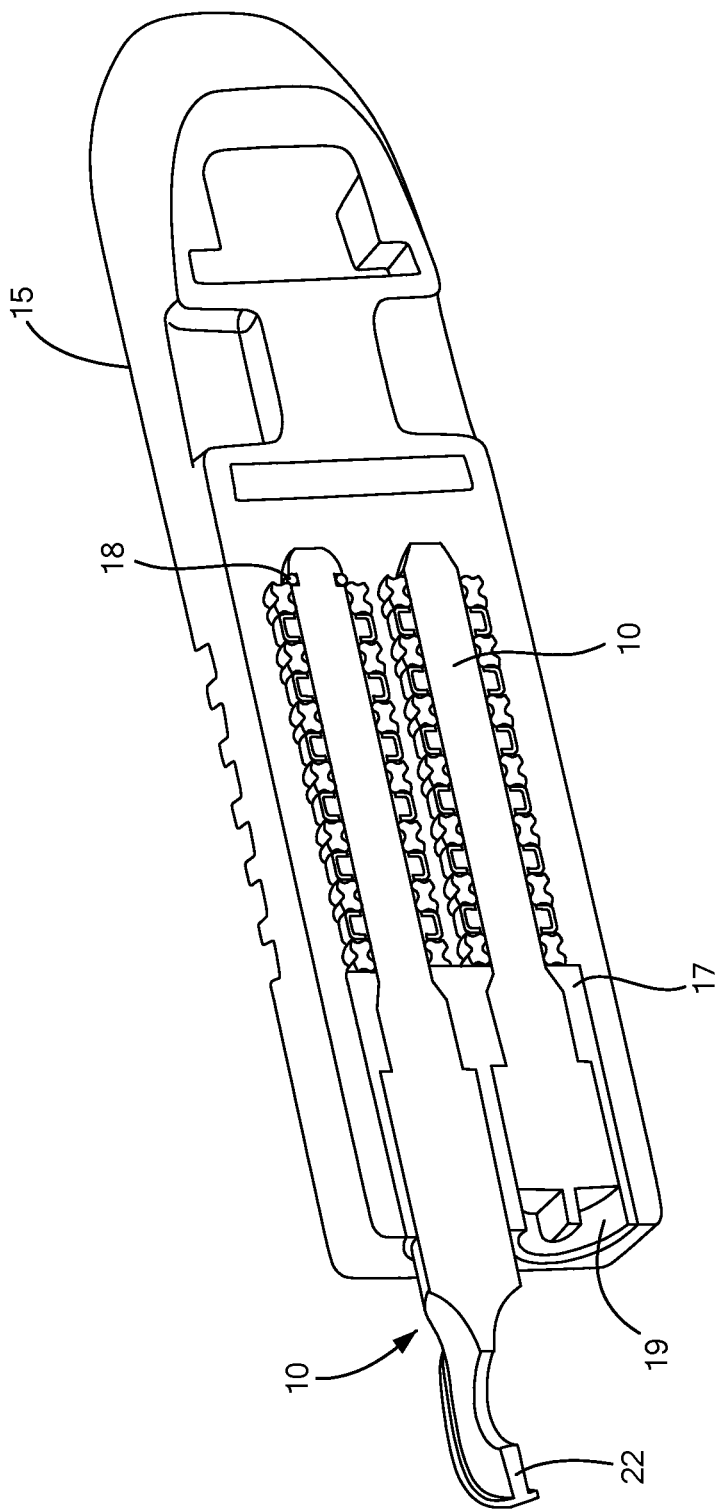
FIG. 2 is a cross-sectional view of the bore plug shown in FIG. 1 within a bore for a header for an implantable medical device.

Referring now to the drawings in which like reference designators refer to like elements, there is shown in FIG. 1 an exemplary bore plug for an implantable medical device constructed in accordance with the principles of the present application and designated generally as "10." The bore plug 10 includes a solid elongate body 12 having a proximal portion 14, a distal portion 16, and defining a major longitudinal axis therethrough "x." In one configuration, the elongate body 12 is a unitary structure and includes a radiopaque material such that it can be seen under fluoroscopy. In the configuration shown in FIG. 1, the distal portion 16 is sized and configured to be received within a bore of the implantable medical device. For example, implantable medical device, such as pacing devices and controllers for implantable blood pumps include connector bores sized to receive a corresponding connector, whether a connector connected to a blood pump or pacing lead. In an exemplary configuration, the distal portion 16 defines an outer diameter of between 0.10 and 0.20 inches and the proximal portion 14 defines an outer diameter of 0.3 and 0.4 inches. That is, the diameter of the distal portion 16 is less than the diameter of the proximal portion 14. In some configurations, as shown in FIG. 2, the distal portion 16 is sized to have a slight interference fit with the inner diameter of the bore of the implantable medical device, for example a header 15 for an implantable controller. In some configuration, at least a portion of the proximal portion 14 is also sized to be received within the bore for the implantable medical device. In particular, some implantable medical devices include a header block end cap 17 defining an end cap bore 19 in communication with the bore of the medical device, and the proximal portion 14 is sized to be received within the header block end cap bore.

Continuing to refer to FIG. 1, the distal portion 16 includes a lubricating element 18 configured to lubricate the bore when the distal portion 16 is inserted within and/or withdrawn from the bore. In an exemplary configuration, the lubricating element 18 may be a ring or other flexible annular structure disposed proximal to the distal most end of the distal portion 16. For example, as shown in FIG. 1, the lubricating element 18 is configured to extend radially outward from the outer diameter of the distal portion 16. Thus, when the distal portion 16 is either inserted or removed from the bore, the lubricating element 18 wipes the interior of the bore, which includes a header seal and thus lubricates the bore. In one configuration, the lubricating element 18 is impregnated, embedded, or coated with a lubricating element, such as a silicone oil, such that a compression force applied to the lubricating element 18 causes lubrication to be released from the lubricating element 18 as it is inserted and/or withdrawn from the bore. In some configurations, the lubricating element 18 is incorporated as part of the distal portion 16. That is, the entirety of the distal portion 16 includes the lubricating element 18 along its outer diameter to lubricate the bore. As shown in FIG. 2, the distal most end of the distal portion 16 is sized to extend beyond the distal end of the bore such that the lubricating element 18 is substantially flush with a distal end of the bore when the distal portion 16 is fully inserted. In such a configuration, a pulling force applied to the elongate body 12 and retraction of the bore plug 10 causes the lubricating element 18 to wipe the inside of the bore with lubricant.

Continuing to refer to FIG. 1, the proximal portion 14 may include one or more flanges 20 circumferentially disposed about the proximal portion. The flanges 20 may be spaced apart from each other and are configured to grip an interior of the end cap for the header in communication with the bore. Optionally, a relief or groove 22 may also be included within the proximal portion 14 or along the major axis of the distal portion 16 to provide an opening for ethylene oxide gas to penetrate the bore plug 10 and disinfect the bore of the implantable medical device. Extending proximally from the proximal portion may be a gripping element 24. The gripping element 24 may be a flexible handle configured to be gripped by the user to insert and remove the bore plug 10. In one configuration, the gripping element 24 is substantially planar and is disposed substantially orthogonal to the major elongate axis and is larger than the elongate body 12 is diameter. The gripping element 24 may be further configured to twist and flex back to its original shape. This, allows a user to grasp a gripping element 24 and pull on it without grabbing or touching an adjacent bore plug 10. In an exemplary configuration, when the bore plug 10 is fully inserted within the connector bore, only the gripping element 24 extends beyond the bore and the proximal portion 14 and the distal portion 16 are fully inserted within the bore. In other configurations, if a second bore plug 10 is included the two bore plugs may be tethered together.

Figure 3:
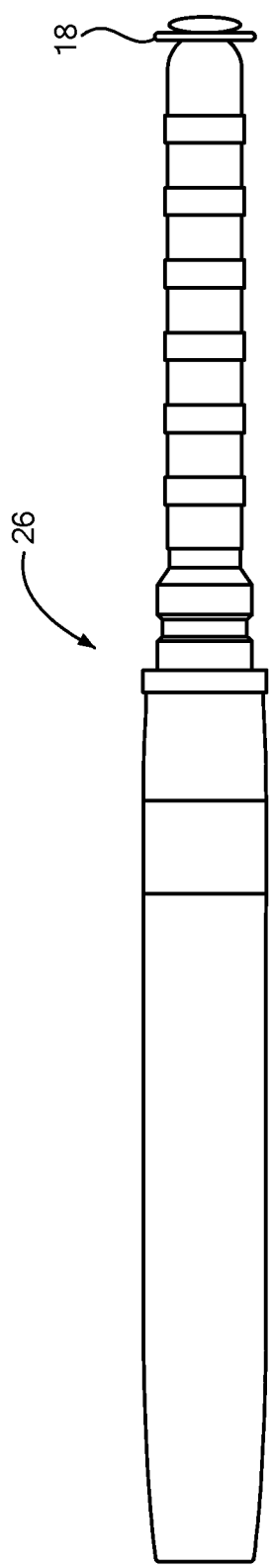
FIG. 3 is a side view of a connector constructed in accordance with the principles of the present application.

Referring now to FIG. 3, in another configuration, a connector 26 of the implantable medical device may including the lubricating element 18 in similar manner to that of the bore plug 10. For example, the connector 26 may include the lubricating element 18, which may be a flexible annular element disposed proximal to the distal most end of the connector 26. In such a configuration, the lubricating element 18 wipes the surface of the bore when it is inserted within the bore. Although described as an annular element, it is further contemplated that the lubricating element 18 may be other shapes and sizes and may be positioned and other locations along the connector 26.

Figure 4:
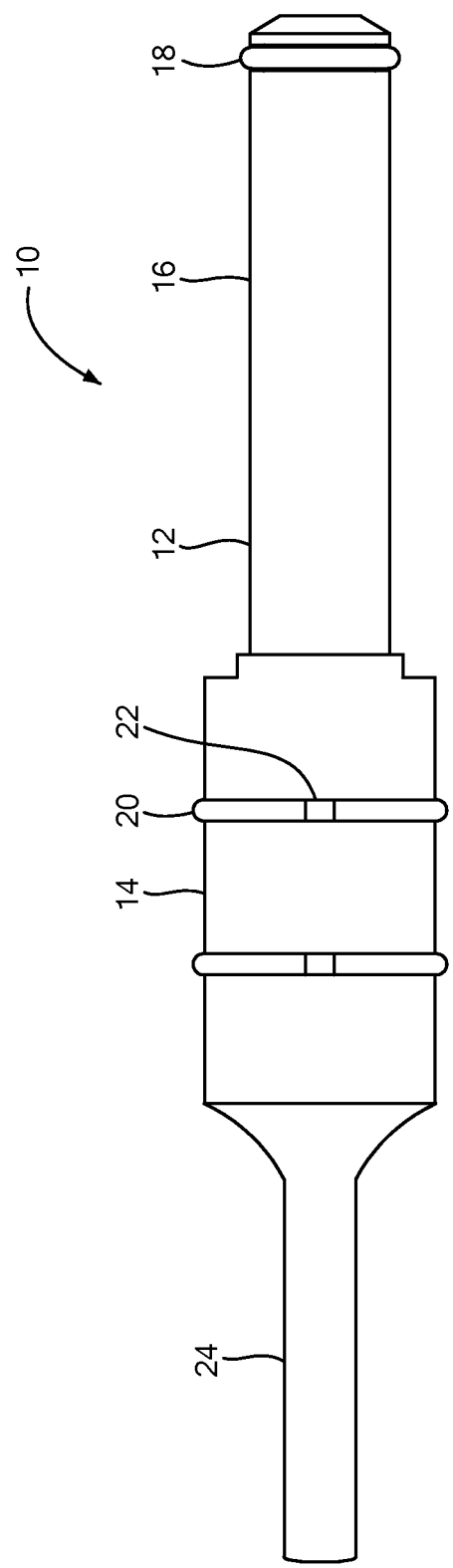
FIG. 4 is a cross-sectional view of another bore plug constructed in accordance with the principles of the present application.

Referring now to FIG. 4, in another configured, bore plug 10 is sized and configured to be received with a housing for an IS-4 or DF-4 connector. In such a configuration, the distal portion 16 may be shorter in length than the distal portion shown in FIG. 1 and the proximal portion 14 may exclude the taper shown in FIG. 1 and may define a wider diameter to that of the configuration shown in FIG. 1. The flanges 20 may be included similar to FIG. 1 and may include reliefs 22 for ETO gas.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. An apparatus comprising:
a medical device defining an end cap bore and a bore that opens to the end cap bore, wherein the end cap bore defines a cross-sectional dimension greater than a cross-sectional dimension of the bore; and
a bore plug comprising an elongate body having a proximal portion, a distal portion, and defining a major longitudinal axis therethrough, the distal portion being sized and configured to be received within the bore, and the proximal portion configured to be received within the end cap bore when the distal portion fully inserts within the bore,
wherein the proximal portion defines a first diameter and the distal portion defines a second diameter less than the first diameter,
wherein the second diameter is configured to cause the distal portion to establish an interference fit with an inner surface of the bore when the distal portion is inserted within or withdrawn from the bore,
wherein the first diameter is configured to limit insertion of the proximal portion into the bore when the distal portion is fully inserted into the bore,
wherein the distal portion includes a lubricating element including a lubricant, the lubricating element configured to wipe the inner surface with the lubricant when the distal portion establishes the interference fit and the distal portion is inserted within or withdrawn from the bore, and
wherein the bore plug includes a gripping element extending proximally from the proximal portion.

2. The apparatus of claim 1, wherein the distal portion comprises of silicone, and wherein the lubricating element comprises the lubricant embedded within at least a portion of the silicone.

3. The apparatus of claim 1, wherein the lubricating element is a flexible ring supporting the lubricant, wherein the flexible ring extends outward from the distal portion.

4. The apparatus of claim 3, wherein the flexible ring is disposed proximal to a distal most end of the distal portion.

5. The apparatus of claim 1, wherein the proximal portion defines at least one of a relief or a groove circumferentially disposed about the proximal portion.

6. The apparatus of claim 5, wherein the at least one of the relief or the groove is configured to provide an opening for a gas to disinfect the bore when the proximal portion is received within the end cap bore and the distal portion fully inserts within the bore.

7. The apparatus of claim 1, wherein the gripping element is flexible.

8. The apparatus of claim 1, wherein the gripping element is configured to extend outside of the bore when the distal portion is fully inserted within the bore.

9. The apparatus of claim 8, wherein the gripping element is configured to extend proximally beyond the end cap bore when the proximal portion is inserted within the end cap bore and the distal portion is fully inserted within the bore.

10. The apparatus of claim 1, wherein the gripping element extends in a direction substantially orthogonal to the major longitudinal axis.

11. The apparatus of claim 1, wherein the elongate body and the lubricating element are formed as a unitary body.

12. The apparatus of claim 1, wherein the proximal portion includes at least one flange surrounding at least a portion of the proximal portion, wherein the at least one flange is configured to grip an interior surface defining the end cap bore when the proximal portion is received within the end cap bore.

13. The apparatus of claim 1, wherein the lubricating element is configured to be substantially flush with a distal end of the bore when the distal portion is fully inserted within the bore.

14. An apparatus comprising:
a medical device defining an end cap bore and a bore that opens to the end cap bore, wherein the end cap bore defines a cross-sectional dimension greater than a cross-sectional dimension of the bore; and
a connector comprising an elongate body having a proximal portion, a distal portion, the distal portion being sized and configured to be received within the bore, and the proximal portion configured to be received within the end cap bore when the distal portion fully inserts within the bore, wherein the elongate body includes a plurality of electrical contacts,
wherein the proximal portion defines a first diameter and the distal portion defines a second diameter less than the first diameter,
wherein the second diameter is configured to cause the distal portion to establish an interference fit with an inner surface of the bore when the distal portion is inserted within or withdrawn from the bore,
wherein the first diameter is configured to limit insertion of the proximal portion into the bore when the distal portion is fully inserted into the bore,
wherein the distal portion includes a lubricating element including a lubricant, the lubricating element configured to wipe the inner surface with the lubricant when the distal portion establishes the interference fit and the distal portion is of inserted within or withdrawn from the bore, and
wherein the connector includes a gripping element extending proximally from the proximal portion.

15. The apparatus of claim 14, wherein the lubricating element is a flexible ring supporting the lubricant, wherein the flexible ring extends outward from the distal portion.

16. The apparatus of claim 15, wherein the flexible ring is disposed distal to the electrical contacts and proximal to a distal most end of the distal portion.

17. An apparatus comprising:
a medical device defining an end cap bore and a bore that opens to the end cap bore, wherein the end cap bore defines a cross-sectional dimension greater than a cross-sectional dimension of the bore; and
a bore plug comprising an elongate body having a proximal portion, a distal portion, and defining a major longitudinal axis therethrough, the distal portion being sized and configured to be received within the bore, and the proximal portion configured to be received within the end cap bore when the distal portion fully inserts within the bore,
wherein the proximal portion defines a first diameter and the distal portion defines a second diameter less than the first diameter,
wherein the second diameter is configured to cause the distal portion to establish an interference fit with an inner surface of the bore when the distal portion is inserted within or withdrawn from the bore,
wherein the first diameter is configured to limit insertion of the proximal portion into the bore when the distal portion is fully inserted into the bore,
wherein the distal portion includes a flexible ring supporting a lubricant, the flexible ring is disposed proximal to a distal most end of the distal portion, and the flexible ring being configured to wipe the inner surface with the lubricant when the distal portion establishes the interference fit and the distal portion is withdrawn from the bore, and a flexible gripping element extending proximally from the proximal portion, the gripping element being configured to twist and retain its original shape, wherein the flexible gripping element is configured to extend outside of the bore when the distal portion is fully inserted within the bore.

18. The apparatus of claim 17, wherein the gripping element extends in a direction substantially orthogonal to the major longitudinal axis.

19. The apparatus of claim 17, wherein the elongate body and the flexible ring are formed as a unitary body.

20. The apparatus of claim 17, further including at least one flange surrounding at least a portion of the proximal portion, wherein the at least one flange is configured to grip an interior surface defining the end cap bore when the proximal portion is received within the end cap bore.

\* \* \* \* \*